United States Patent
Pitter et al.

(10) Patent No.: US 6,291,390 B1
(45) Date of Patent: Sep. 18, 2001

(54) CATALYST OBTAINED FROM PHOSPHINOALKYL-FUNCTIONALIZED POLYSTYRENE AND METHOD FOR THE PRODUCTION OF δ-LACTONE

(75) Inventors: Stephan Pitter; Eckhard Dinjus, both of Jena; Nancy Holzhey, Kahla, all of (DE)

(73) Assignee: Forschungszentrum Karlsruhe (DE)

( * ) Notice: Subject to any disclaimer, the term of this patent is extended or adjusted under 35 U.S.C. 154(b) by 0 days.

(21) Appl. No.: 09/446,243

(22) PCT Filed: Jun. 2, 1998

(86) PCT No.: PCT/EP98/03290

§ 371 Date: Apr. 10, 2000

§ 102(e) Date: Apr. 10, 2000

(87) PCT Pub. No.: WO98/57745

PCT Pub. Date: Dec. 23, 1998

(30) Foreign Application Priority Data

Jun. 18, 1997 (DE) .............................................. 197 25 735

(51) Int. Cl.$^7$ ..................... B01J 27/185; C07D 309/00
(52) U.S. Cl. ............................................ 502/213; 549/273
(58) Field of Search ............................. 549/273; 502/213

(56) References Cited

U.S. PATENT DOCUMENTS 4,506,030   3/1985   Jones .
5,498,582 * 3/1996   Krause et al. ........................ 502/103
5,525,566 * 6/1996   Keim et al. ............................ 502/162

FOREIGN PATENT DOCUMENTS 28 38 610 A1   3/1979   (DE) .
0 234 668 A2   9/1987   (EP) .

OTHER PUBLICATIONS

Stephan Pitter, et al, "Phosphinoalkylnitrile: Synthese und Koordinationsverhalten an Palladiumzentren", *Naturforsch*, 1996, 51b, pp. 934–946.

Kaneda, et al, "Selective Telemerization of Butadiene with Various Nucleophiles Catalyzed by Polymer–Bound Palladium (0) Complexes", *J. Org. Chem* 1981, vol. 46, pp. 2356–2362.

* cited by examiner

*Primary Examiner*—Deborah C. Lambkin
(74) *Attorney, Agent, or Firm*—Venable; Norman N. Kunitz; Ashley J. Wells

(57) ABSTRACT

The invention relates to the reaction of 1,3-butadiene and carbon dioxide. The invention aims at providing a catalyst for said reaction, which can be easily recovered and does not contaminate the final product. The invention also relates to a method for producing δ-lactone. According to the invention, a phosphinoalkyl-functionalized polystyrene is used to produce such a catalyst. The catalyst can be obtained by reacting phosphinoalkyl-functionalized polystyrene with ($\eta^5$-cyclopentadienyl) ($\eta^3$-allyl)palladium. The catalyst is used in the method to produce δ-lactone.

4 Claims, No Drawings

CATALYST OBTAINED FROM PHOSPHINOALKYL-FUNCTIONALIZED POLYSTYRENE AND METHOD FOR THE PRODUCTION OF δ-LACTONE

This application is a 371 of PCT/EP98/03290 Jun. 2, 1998.

BACKGROUND OF THE INVENTION

The invention relates to a catalyst obtained from phosphinoalkyl-functionalized polystyrene, in accordance with the first patent claim and a method for producing δ lactone according to the preamble to the third patent claim.

DESCRIPTION OF THE RELATED ART

The use of phosphinoalkyl-functionalized polystyrene for producing a catalyst that catalyzes conversions of 1,3-butadiene with nucleophiles is known from the reference Kaneda et al. "Selective Telomerization of Butadiene with Various Nucleopphiles Catalyzed by Polymer-Bo- and Palladium (0) Complexes," J. Org. Chem. 1981, 46, 2356–2362.

The article by Stephan Pitter, Eckhard Dinjus, Beate Jung and Helmar Gorlis: "PHOSPHINOLALKYLNITRILE: SYNTHESE UND KOORDINATIONS-VERHALTEN AN PALLADIUMZENTREN [Phosphinoalkyl Nitriles: Synthesis and Coordination Behavior on Palladium Centers]," published in the magazine Naturforsch. 51b, pp 934–946 (1996), dicloses that the synthesis of the δ-lactone (2-ethylidene-hepta-6-en-5-olide) is catalyzed with high selectivity through Pd(0) complexes with wide-spreading phosphine ligands. A phosphinoalkyl nitrile of the type $R_2P\text{—}(CH_2)n\text{—}CN$ (n=1) is used as a preliminary stage for displaying the catalysts, wherein chain lengths with n>4 are preferred for steric reasons. The phosphinoalkyl nitrile is converted with a palladium (II)-compound, e.g. ($\eta^5$-cyclopentadienyl) ($\eta^3$-allyl) palladium. The synthesis of the δ lactone thus occurs with a homogeneous catalysis and the use of a solvent.

European Patent 0 234 668 A2 discloses the production of δ lactone by converting 1,3-butadiene with carbon dioxide in a solvent, in the presence of palladium or a palladium compound, an amine and a bidentate ligand with the general formula $R^1R^2MRMR^3R^4$, wherein M, for example, is phosphor, R is an organically bridging group with 3C-atoms, and $R^{1-4}$ are substituted or non-substituted hydrocarbon groups.

German Patent 28 38 610 A also discloses a method for producing δ lactone from 1,3 butadiene and carbon dioxide. With this method, the two base materials are converted in the presence of a catalyst in the form of a palladium phosphine complex with the formula Pd $[P(R)_3]_x$, wherein x represents a whole number from 2 to 4 and R represents an alkyl residue or a cycloalkyl residue with up to 8 carbon atoms or a phenyl residue. The residues can also be substituted and can be the same or different. The process temperature provided is 20° to 150° C. and the total pressure 10 to 500 bar. The catalyst can be produced in situ by adding its educts, a palladium compound and a phosphine, to the reaction medium.

The known methods with homogeneous catalysis have several disadvantages. The catalyst cannot be recaptured, so that the expensive base materials must be provided again for each conversion. In addition, the catalyst and its decomposition products contaminate the desired end product.

It is the object of the invention to remove these disadvantages and to use a catalyst for the conversion of butadiene with carbon dioxide, which can be recaptured easily and does not contaminate the end product. In addition, another method for producing δ lactone is to be suggested.

SUMMARY OF THE INVENTION

This object is accomplished by providing a catalyst, obtained through a conversion of phosphinoalkyl-functionalized polystyrene with ($\eta^5$-cyclopentadienyl)($\eta^3$-allyl) palladium. Preferably, the catalyst is obtained through a conversion with (diisopropylphosphino) methyl-functionalized polystyrene. The object of the present invention is likewise accomplished by providing a method for producing δ lactone, for which 1,3-butadiene is converted with carbon dioxide in the presence of the catalyst, wherein the catalyst used is the product of the reaction of ($\eta^5$-cyclopentadienyl)($\eta^3$-allyl) palladium with a compound containing a phosphino group, characterized in that the compound containing a phosphino group is a phosphinoalkyl-functionalized polystyrene.

According to the invention, an optional phosphinoalkyl-functionalized polystyrene is used for producing the catalyst, wherein it is not important at which intervals the phenyl groups suspended from the polymer skeleton are substituted. A straight-chain or a branched alkyl residue, for example with 2 to 8 carbon atoms, with a cycloalkyl residue or an aryl residue can be used for a phosphino group substitution. Preferred is the substitution with an isopropyl residue.

The phosphinoalkyl-functionalized polystyrene (2) can be produced, for example, with the following reaction of commercially available, partially chloromethylated polystyrene (1):

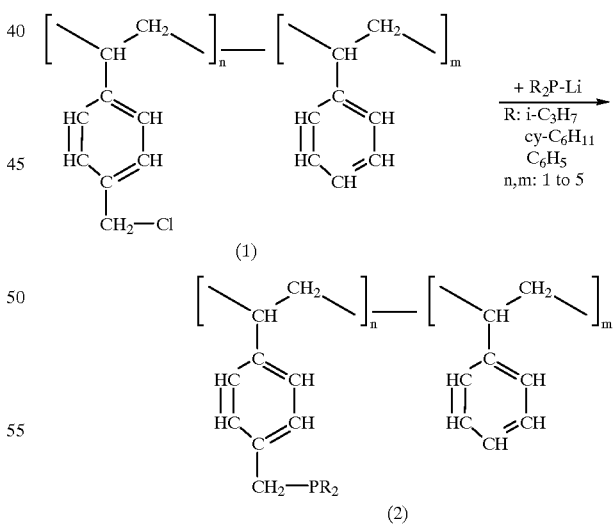

where R is an alkyl, aryl or cycloalkyl, preferably isopropylene, and n and m represent identical or different whole numbers ranging from 1 to 5.

For the production of the catalyst, the phosphinoalkyl-functionalized polystyrene is converted with ($\eta^5$-cyclopentadienyl)($\eta^3$-alkyl) palladium (3).

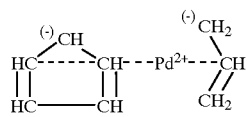

(3)

The allyl can be substituted, e.g. with allyl chains having a length of 1 to 10 C-atoms. The cyclopentadienyl residue can be substituted in the same way. However, non-substituted allyl ($C_3H_5$) is preferred. The conversion can take place "in situ" in the presence of the reactants or can occur prior to the reaction. The second alternative opens up the option, which is not provided in prior art, of using a pre-prepared catalyst.

The reactor is filled in the presence of a protective gas atmosphere (nitrogen, argon). The reaction is carried out without the presence of air and moisture, in a carbon dioxide atmosphere and at a temperature of between 25° and 90° C., preferably at 60° to 70° C. and a pressure of 5 to 100 bar, preferably at 20 to 30 bar. The reaction takes from 2 to 50 h.

The catalyst prepared "in situ" as well as the pre-prepared catalyst can be used repeatedly. The activity of the pre-prepared catalyst is initially higher, but drops after several cycles to values that are comparable to those of the in situ generated catalyst. The selectivity in the formation of 2-(E)-ethylidene-hepta-6-en-5-olide is between 57 and 71% for reaction times that are not excessively long.

The alternatively accessible products according to Pitter et al and the literature cited therein ($C_{17}$-ester, γ lactone etc.) can also be produced with the catalyst system described therein (for example with noticeably longer reaction times).

The invention offers a series of advantages: The catalyst can be easily separated from the reaction mixture through filtration and can be regenerated by simply washing and drying it. Alternatively, the catalyst can be provided in a strainer. With respect to the use of the expensive butadiene, it shows a high selectivity in the range between 50 and 75%, so that butadiene losses caused by conversion to by-products are low. The end product is not contaminated with the catalyst or its decomposition products. The method can thus be carried out continuously.

DESCRIPTION OF THE PREFERRED EMBODIMENT

In the following, the invention is explained in further detail with the aid of test examples.

In all cases, the catalyst used was ($\eta^5$-cyclopentadienyl)($\eta^3$-allyl) palladium. The solvent used was acetonitrile. The reaction conditions were 16 hours at approximately 70° C.

All experiments were carried out in a 250 ml stainless steel autoclave, equipped with gas inlet and gas outlet valves, manometer, inside thermometer, magnetic stirring rods and heated magnetic stirrer. The specified reaction temperatures were adjusted by means of an oil bath. In order to be able to compare the individual experiments within a series, with respect to the selectivity to δ lactone, the reaction times were selected such that a complete conversion of butadiene has not yet taken place.

EXAMPLE 1
Catalyses with In Situ Generated Catalyst 227.6 mg [(diisopropylphosphino)methyl]polystyrene (with 0.333 mmol bonded phosphor) were stirred up in 20 ml acetonitrile and transferred by means of a PTFE cannula into the autoclave. Subsequently, 36.8 mg (η5-cyclopentadienyl)($\eta^3$-allyl) palladium (0.173 mmol), dissolved in 10 ml acetonitrile were also added with a PTFE cannula. After the autoclave has been cooled down to −30° C., 13.5 g of 1,3,butadien (0.25 mmol) are added as condensate by way of a stainless steel line. The autoclave is heated up to 25° C. Following this, 13.2 g $CO_2$ (0.3 mol) are pressed on. The autoclave is subsequently tempered to 70° C., wherein the inside pressure rises to 25 to 27 bar. The mixture is stirred with 500 rotations/minute. Following a reaction time of 16 hours, the reactor is cooled down outside of the oil bath to 25° C. and the excess pressure let off carefully over a period of 30 minutes via an exhaust gas line. The reaction solution, which is normally yellow, is separated from the polymer catalyst by filtering it through a G4 frit. After concentrating the reaction solution to small volume at 40° C. in the oil pump vacuum, a weighing out occurs and the Ŭ lactone yield is determined with the aid of HPLC. The separated out catalyst is then washed twice with respectively 10 ml acetonitrile, is transferred to a swiveling vessel and is freed of solvent residues in a vacuum at 25° C. Subsequently, it can be reused for other catalyses.

All other catalyses can be carried out analog to the above-described process sequence, with the exception that the dried, heterogeneous catalyst from previous experiments is absorbed in 30 ml acetonitrile and is transferred by means of a PTFE cannula to the autoclave. The two rows of experiments, listed in the following, were carried out under identical conditions and demonstrate the good reproducibility of the method.

|  | weight of raw product in [g] | selectivity in [%] |
|---|---|---|
| Experimental series 1 |  |  |
| 1st use of catalyst: | 2,413 | 57 |
| 2nd use of catalyst: | 1,326 | 64 |
| 3rd use of catalyst: | 1,126 | 71 |
| 4th use of catalyst: | 1,117 | 66 |
| 5th use of catalyst: | 0,928 | 63 |
| Experimental series 2 |  |  |
| 1st use of catalyst: | 2,513 | 60 |
| 2nd use of catalyst: | 1,459 | 65 |
| 3rd use of catalyst: | 1,011 | 61 |
| 4th use of catalyst: | 1,100 | 67 |
| 5th use of catalyst: | 0,976 | 64 |
| Long-term experiment: |  |  |
| 232.5 hours at 73–75° C. | 9,520 | 38 |

EXPERIMENT 2
Catalyses with Pre-prepared Catalyst

For the pre-preparation of a catalyst from [(diisopropylphosphino)methyl]polystyrene and ($\eta^5$-cyclopentadienyl)($\eta^3$-allyl) palladium, 36.8 mg [$\eta^5$-cyclopentadienyl)($\eta^3$-allyl) palladium (0.173 mmol) dissolved in 10 ml acetonitrile are added to 227.6 mg [(diisopropylphosphino)methyl]polystyrene(with 0.333 mmol bonded phosphor) in 20 ml acetonitrile by stirring the mixture strongly at 25° C. The reaction mixture is kept at 60° C. for four hours. Subsequently, the mixture is cooled down to 25° C., the catalyst is filtered off and is washed five times with respectively 25 ml acetonitrile. Following the drying in the oil pump vacuum at 25° C., a dark brown solid material is obtained.

The catalyst, which is stirred into 30 ml acetonitrile, is transferred by means of a PTFE cannula to the autoclave. The further reaction then occurs analog to the process sequence in example 1.

|  | weight of raw product in [g] | selectivity in [%] |
|---|---|---|
| 1st use of catalyst: | 4,692 | 56 |
| 2nd use of catalyst: | 1,953 | 68 |
| 3rd use of catalyst: | 1,376 | 72 |
| 4th use of catalyst: | 1,211 | 71 |
| 5th use of catalyst: | 0,949 | 66 |
| Long-term experiment: | | |
| 232 hours at 73–75° C. | 9,558 | 37 |

What is claimed is:

1. A method for producing δ lactone, comprising:
   providing a catalyst by reacting ($\eta^5$-cyclopentadienyl) ($\eta^3$-allyl) palladium with a compound containing a phosphino group which is a phosphinoalkyl-functionalized polystyrene; and
   converting 1,3-butadiene with carbon dioxide in the presence of the catalyst.

2. A method for producing a catalyst, comprising:
   reacting ($\eta^5$-cyclopentadienyl) ($\eta^3$-allyl)palladium with a compound containing a phosphino group which is a phosphinoalkyl-functionalized polystyrene.

3. A catalyst, obtained through a conversion of phosphinoalkyl-functionalized polystyrene with ($\eta^5$-cyclopentadienyl) ($\eta^3$-allyl)palladium.

4. The catalyst according to claim 1, obtained through a conversion with (diisopropylphosphino) methyl-functionalized polystyrene.

\* \* \* \* \*